United States Patent [19]

Kamijo et al.

[11] Patent Number: 4,931,405
[45] Date of Patent: Jun. 5, 1990

[54] METHOD FOR MANUFACTURING A SEMICONDUCTOR DEVICE AND SUPPRESSING THE GENERATION OF BULK MICRODEFECTS NEAR THE SUBSTRATE SURFACE LAYER

[75] Inventors: Hiroyuki Kamijo, Yokohama; Yuuichi Mikata, Kawasaki, both of Japan

[73] Assignee: Kabushiki Kaisha Toshiba, Kawasaki, Japan

[21] Appl. No.: 306,716

[22] Filed: Feb. 6, 1989

[30] Foreign Application Priority Data

Feb. 8, 1988 [JP] Japan .................................. 63-26917

[51] Int. Cl.$^5$ .......................................... H01L 21/265
[52] U.S. Cl. .......................................... 437/12; 437/24; 437/26; 437/29; 437/47
[58] Field of Search .................... 437/20, 24, 26, 28, 437/29, 11, 47, 52, 69, 70, 72, 12

[56] References Cited

U.S. PATENT DOCUMENTS 4,762,802  8/1988  Parrillo ................................. 437/24

FOREIGN PATENT DOCUMENTS 131717     1/1985  European Pat. Off. .
58-39014   3/1983  Japan .................................. 437/20
59-56575   4/1984  Japan .................................. 437/20
59-108366  6/1984  Japan .................................. 437/20
60-39824   3/1985  Japan .................................. 437/20
62-210627  9/1987  Japan .

OTHER PUBLICATIONS

Journal of the Electrochemical Society, vol. 134, No. 4, Apr. 1987, pp. 1018–1025, L. Jastrzebski et al.
IEEE Electron Device Letters, vol. EDL-6, No. 12, Dec. 1985, pp. 659–661, S. S. Wong.
Extended Abstracts, vol. 86-1, No. 1, May, 1986, Abstract No. 197, pp. 283–284.

Primary Examiner—Olik Chaudhuri
Attorney, Agent, or Firm—Finnegan, Henderson, Farabow, Garrett and Dunner

[57] ABSTRACT

A method for manufacturing a semiconductor device is disclosed which selectively forms in a one-conductivity type semiconductor device a deep impurity-diffused area at over 1100° C. in an $H_2$ gas atmosphere containing $N_2$, Ar, Ne, He and a combination thereof.

4 Claims, 5 Drawing Sheets

DIFFUSION CONDITIONS·
1200°C, 3HOURS
$N_2/H_2$ MIXED GAS ATMOSPHERE

DIFFUSION
CONDITIONS:
1200°C, 3HOURS
$N_2/H_2$ MIXED GAS
ATMOSPHERE

METHOD FOR MANUFACTURING A SEMICONDUCTOR DEVICE AND SUPPRESSING THE GENERATION OF BULK MICRODEFECTS NEAR THE SUBSTRATE SURFACE LAYER

BACKGROUND OF THE INVENTION

1. Field of the Invention

The present invention relates to a method for manufacturing a semiconductor device having a deep impurity diffusion area, such as a well area, in a semiconductor substrate, which can enhance the gettering of a metal impurity in the semiconductor substrate during a thermal diffusion step of a wafer process.

2. Description of the Related Art

In order to getter, for example, a metal impurity during the manufacturing of a conventional semiconductor device, use is made of a phosphorus getter containing phosphor glass ($P_2O_5$) or intrinsic gettering method (IG).

In the IG method, microdefects are formed in a wafer, without using a separate operation, giving the wafer a getting capability.

A silicon crystal which is grown in a CZ (Czochralski) method is usually employed for an LSI element substrate. In recent times, use is also made of an Si crystal grown by a magnetic application type CZ (MCZ) method. The wafer obtained by the above method as grown from a crucible contains supersaturated oxygen extracted and from the atmosphere during crystal growth. Such excess oxygen in a crystal reacts with a portion of the silicon in a thermal process to form an oxide precipitate. Its value change is about twice, and the excess silicon atoms are emitted as self-interstitials. And the excess silicon atoms form dislocations and stacking faults. In general, these oxide precipitate dislocations and stacking faults are called BMD (Bulk Microdefect). The BMD functions as the center of gettering and is capable of gettering, for example, a metal impurity.

The IG method utilizes the gettering capability of the BMD. That is, the IG method achieves a gettering function by out-diffusing oxygen by a heat treatment near the surface of a wafer element formation area to form a denuded zone (DZ) of a predetermined width and to distribute a high-density BMD in an internal region where no element is to be formed.

The IG method will be explained below in connection with a complementary MOS having a well area by referring to FIGS. 1A to 1C.

FIGS. 1A to 1C are cross-sectional views showing the main behavior of oxygen in one form of model. In the case of a complementary type semiconductor device, in order to form a deep P- or N- well in the initial phase of the manufacturing process, an impurity is thermally diffused in the surface of wafer 1 for hours at a temperature of over 1100° C. Of the oxygen in the wafer indicated by small dashes, surface layer oxygen is out-diffused during this step to form defect-free layer 2 (DZ of a predetermined width) in the surface portion of the substrate as shown in FIG. 1A. During the steps of forming a nitride film by a vacuum CVD method, the wafer is heat treated at 600° to 800° C. to form oxygen precipitate nuclei (X in FIG. 1B) in intermediate layer 3 in the wafer as shown in FIG. 1B. During the steps of forming a field oxide film, the wafer is heat treated at about 1000° C. and the nuclei allow precipitates to be grown therabout, forming gettering zone 4 where BMDs are distributed in high density as indicated by marks in FIG. 1C.

The generation of oxygen precipitates and hence the BMD is largely varied, depending upon not only the heat history but also the carbon density, pulling condition during the growth of a crystal, and so on. At the present time, a possible nucleus of the BMD is regarded as being an oxygen microdeposit upon the pulling of the crystal and, those nuclei, exceeding their critical size, are grown into BMDs. The critical size differs, depending upon the temperature, and the lower the temperature, the smaller the precipitate is grown from the nucleus. The precipitates of varying size and number are dispersed within the wafer.

In the semiconductor device manufactured using the IG method, an element is formed in the DZ, but the conventional technique encounters a problem that the electrical characteristics of elements become poor due to the presence of crystal defects near the wafer surface layer.

Generally, diffusion occurs in the well at a temperature as high as over 1100° C. and the solid solution limitation of the oxygen becomes higher, and the critical size of the precipitate nucleus becomes larger. In view of the above, the behavior of the oxygen near the wafer surface layer is regarded as being an "out-diffusion", but it has been found that, if the precipitate nucleus exceeds the critical size at a prevailing temperature during the diffusion of the well, a lower density of defects are grown into BMDs at the wafer surface layer.

FIG. 2 shows a relation of the surface density (number/$cm^2$) of the BMD to the depth ($\mu m$) from the wafer surface which is obtained from a wafer of an oxygen concentration $1.7 \times 10^{18}$ atoms/$cm^3$—a value obtained by finding the absorption coefficient $\alpha$ ($cm^{-1}$) of an infrared radiation with a wave number of 1106 $cm^{-1}$ and calculating an equation $\alpha \times 4.81 \times 10^{17}$ atoms/$cm^3$—by, subsequent to performing a heat treatment in an $N_2$ atmosphere at 1200° C. for 3 hours, carrying out a heat treatment in the $N_2$ atmosphere at 1000° C. for 20 hours. FIG. 3 is a graph showing a relation of an oxygen concentration (atoms/$cm^3$) to the depth ($\mu m$) from the surface of a wafer which was heat treated at 1200° C. for 3 hours as examined by a secondary ion mass spectrometry (SIMS). From FIGS. 2 and 3 it has been found that the out-diffusion of oxygen occurs from a considerably deep position, but that BMDs occur from a relatively shallow position. It has also been found that BMDs generated from a shallow position near the surface of the wafer present dislocation nuclei as generated upon the isolation of elements when an LOCOS method is employed, or the generation center or recombination center of carriers, to adversely affect the electrical characteristics of the elements.

SUMMARY OF THE INVENTION

It is accordingly the object of the present invention to provide a method for manufacturing a semiconductor device having, in a semiconductor substrate of one conductivity type, deep island-like diffusion layers of the opposite conductivity type, which can provide an adequate IG effect and suppress the generation of BMDs near the surface layer, which would otherwise occur in a conventional IG method, and hence improve the characteristics and yield of the semiconductor device.

In order to achieve the aforementioned object of the present invention, a method for manufacturing a semiconductor device is provided which includes the steps of selectively forming in a one-conductivity type semiconductor device a deep impurity-diffused area of the other conductivity type, comprising the steps of:
(a) forming an oxide film on the semiconductor substrate;
(b) performing a resist patterning on the oxide film;
(c) implanting an impurity ion at a predetermined location, subsequent to the patterning step, at over 1100° C. in a $H_2$ gas atmosphere containing $N_2$, Ar, Ne, He or a combination thereof; and
(d) removing the oxide film left.

According to the present invention, it is possible to largely suppress the generation of BMDs still present near the surface layer when a conventional IG method is employed in order to obtain a defect-free layer of an adequate DZ. It is also possible to form a gettering portion of a high-density BMD distribution. Furthermore, the formation of nuclei due to $O_2$ penetrating the oxide film of the semiconductor substrate can be prevented, thus obtaining highly reliable characteristics and hence a high manufacturing yield.

DETAILED DESCRIPTION OF THE PREFERRED EMBODIMENTS

A method for manufacturing a semiconductor device will be explained below with reference to FIGS. 4 to 9.

Figure 1A:
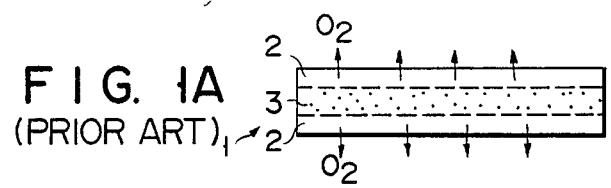
FIGS. 1A to 1C are cross-sectional views showing the function of an IG on a complementary type semiconductor device as manufactured in a conventional method.
Figure 1B:
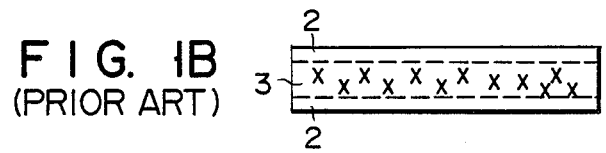
Figure 1C:
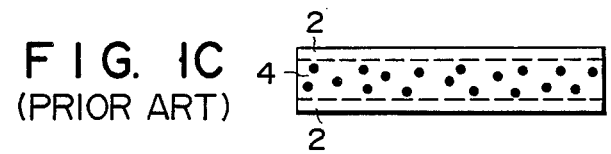
Figure 2:
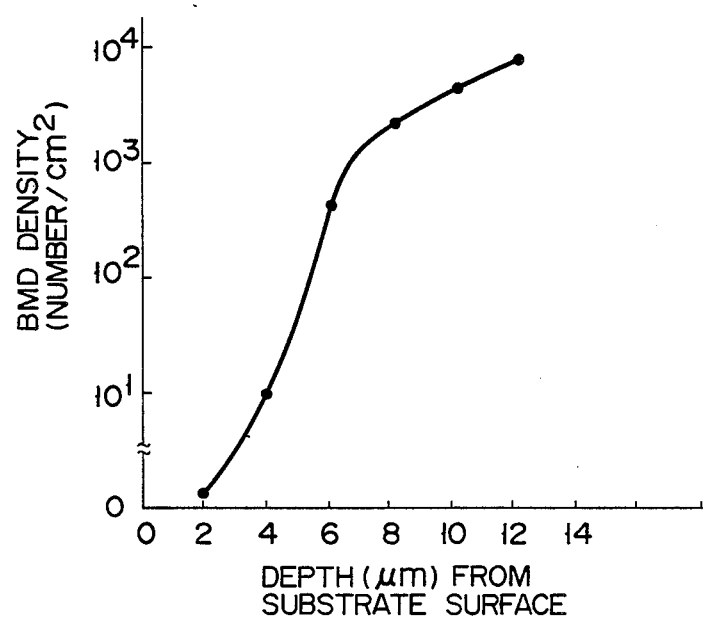
FIG. 2 is a graph showing a relation of a surface density (number/$cm^2$) of BMDs to a depth ($\mu m$) from a well surface as known in the conventional IG method.
Figure 3:
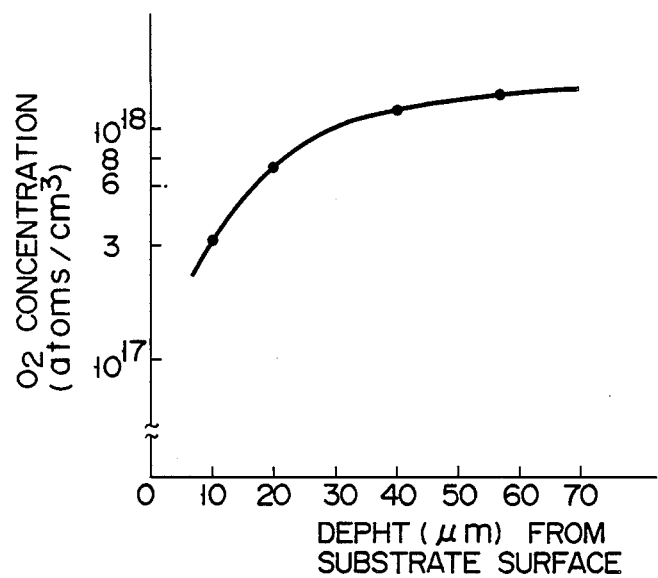
FIG. 3 is a graph showing an $O_2$ concentration (atoms/$cm^3$) to a depth ($\mu m$) from a wafer surface obtained, after performing a heat treatment, in accordance with the conventional IG method.
Figures 4A, 4B:
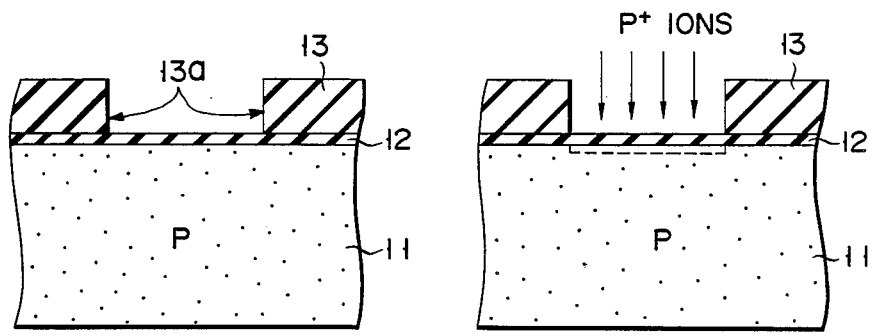
FIGS. 4A to 4E are cross-sectional views illustrating the process of forming a field region of a semiconductor device manufactured in accordance with the present invention.
Figure 4C:
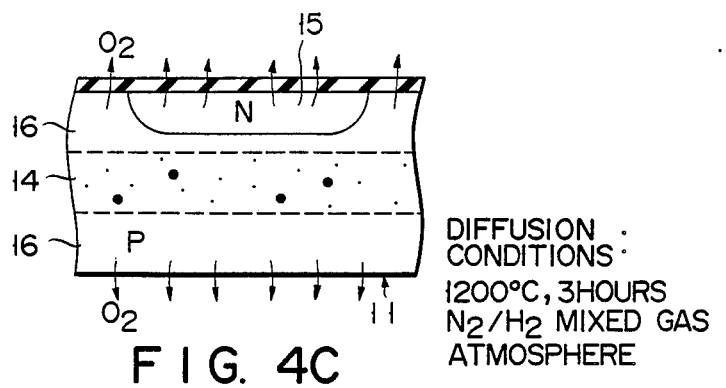
Figure 4D:
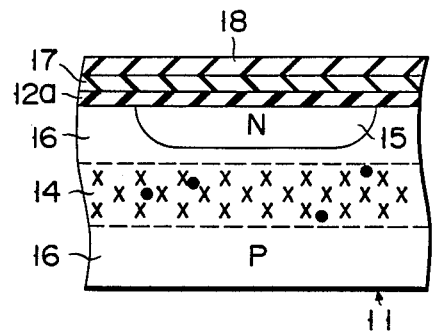
Figure 4E:
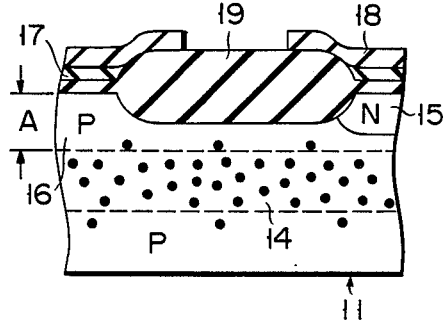

FIGS. 4A to 4E are partial, cross-sectional views showing the manufacture of a dynamic random access memory (DEAM) including CMOSs as elements. A 1000 Å-thick oxide film ($SiO_2$ film) 12 is formed on P type semiconductor substrate 11 and, subsequent to coating resist film 13, diffusion window 13a for N well area formation is provided, as shown in FIG. 4A, with the use of a known lithography technique. In this case, as the wafer use may be made of a P type wafer with a diameter of 125 mm, a specific resistance of 4 to 6 $\Omega cm$ and an oxygen concentration of 1.7 to $1.8 \times 10^{18}$ atoms/$cm^3$. The oxygen concentration is found from an equation $$\alpha \times 4.81 \times 10^{17} \text{ atoms/cm}^3$$

with the use of the absorption efficient $\alpha$ ($cm^{-1}$) of an infrared radiation whose wave number is 1106 $cm^{-1}$. A phosphorus (donor impurity P) ion is implanted into a resultant semiconductor structure at an acceleration voltage of 150 KeV and a dose of $1 \times 10^{13}$ atoms/$cm^2$ as shown in FIG. 4B. The structure is heat treated at 1200° C. for three hours in a gaseous $N_2/H_2$ (=20l/2l) atmosphere to form N well 15 about 3 $\mu m$ deep. At this time, the diffusion of the well is carried out with an oxide left to prevent roughening of the wafer surface (see FIG. 4C). The oxygen near the surface of the substrate is out-diffused by the aforementioned heat treatment and oxygen deposits (mainly $SiO_2$) near the wafer surface are reduced by $H_2$ in a gaseous atmosphere and released. By so doing, the oxygen and BMD concentration near the surface of the substrate are decreased prominently to form a defect-free zone (DZ layer) 16. In order to form a field oxide film for element isolation by the LOCOS method, oxide film 12a is formed on substrate 11 and then poly-Si film 17 and silicon nitride ($Si_3N_4$) 18 are deposited by a vacuum CVD (LPCVD) on the semiconductor substrate at a substrate temperature of 600° to 800° C. for about 6 hours to allow oxygen to be precipitated within the substrate. As a result, very small nuclei (X in FIG. 4D) are formed, in high density, in intermediate layer 14 as shown in FIG. 4D, noting that the nuclei are assumed to be a few angstroms to tens of angstroms. Then a window is opened in a field oxide film formation area for element isolation and the structure is heat treated in a wet atmosphere at about 1000° C. for about 5 hours to form thick field oxide film 19 at an element isolation area alone (see FIG. 4E). By this heat treatment, the precipitated nuclei marked "X" in FIG. 4D are grown into micro-defects (BMD) so that the intermediate layer becomes gettering portion 14 having a gettering capability. Elements, such as PMOSs and NMOSs are formed within defect-free layer 16 of a DZ width A to form a DRAM. In the manufacturing of the semiconductor device, substrate 11 is heat treated several times and hence the nuclei (marked "X") are grown into BMDs each time, allowing metal impurities to be gettered up to a final phase of the manufacturing process.

Figure 5:
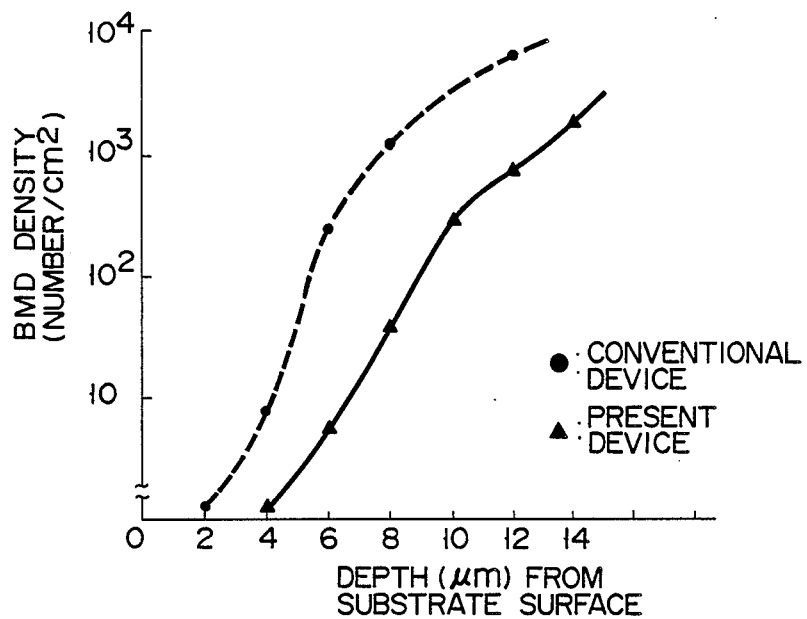
FIG. 5 is a comparison graph showing a relation of a BMD's density distribution to a depth from a substrate surface of a DRAM using a well drive-in of the present invention and that using a conventional well diffusion method.
Figure 6:
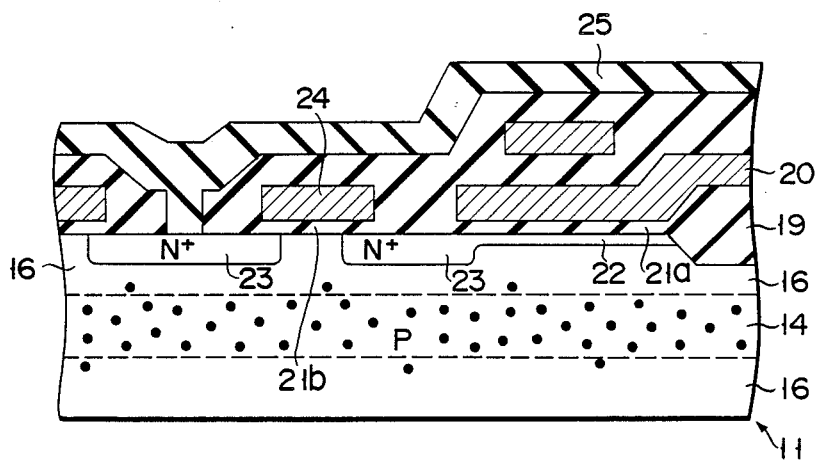
FIG. 6 is a cross-sectional view showing, as a model, a cell structure portion of a DRAM as a semiconductor structure of the present invention.
Figure 7:
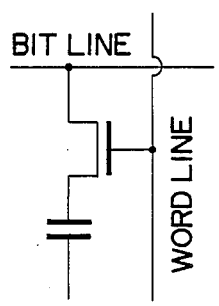
FIG. 7 shows an equivalent circuit diagram of a DRAM as illustrated in FIG. 6.
Figure 8:
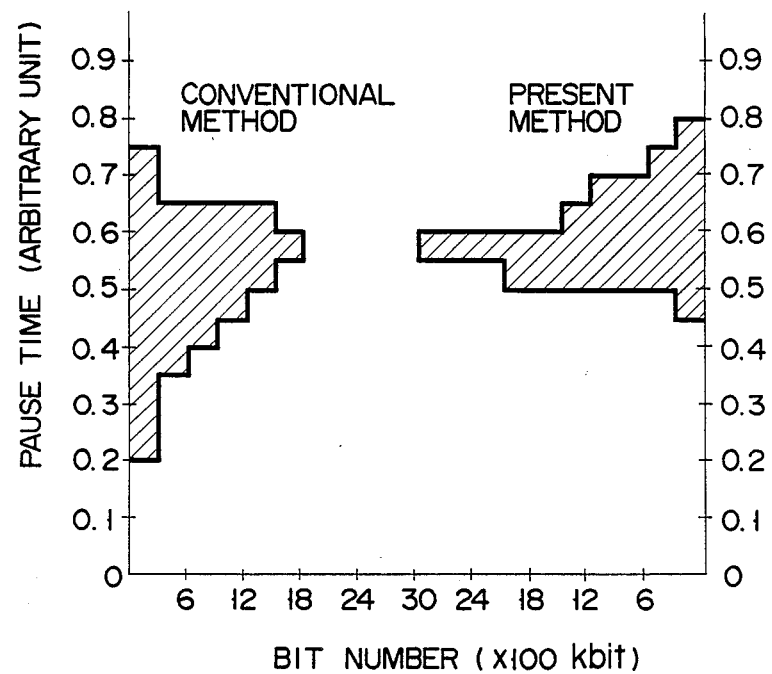
FIG. 8 is a comparison graph showing a relation of a bit number to the pause time of respective bits of one chip of a semiconductor device manufactured in accordance with the conventional method and the method of the present invention.

FIG. 5 shows the relationship between the BMD density destribution and the depth from the surface of a substrate in a DRAM manufactured by the aforementioned well diffusion method of the present invention and in a DRAM manufactured in a conventional well diffusion method using an $N_2$ or an $N_2/O_2$ mixed gas atmosphere, noting that the wafer is sliced from the same area of the same ingot. In FIG. 5, the solid curve and dotted curve show the characteristic of the semiconductor device of the present invention and that of the conventional semiconductor device. From FIG. 5 it is seen that the BMD density itself is somewhat decreased in the semiconductor device of the present invention, but that the depth from the substrate surface at which the BMDs occur is deeper in the semiconductor device of the present invention than the conventional semiconductor device. That is, according to the method of the present invention, it is possible to obtain a deeper DZ zone. 1 M-bit CMOS DRAMs were manufactured in accordance with the method of the present invention and conventional method, using a wafer of the same area sliced from the same ingot. The CMOS DRAMs were examined for a variation in the charge retaining time (pass time) of capacitors within one chip. FIG. 6 is a cross-sectional view showing a model of a DRAM cell structure comprising one MOS capacitor and one transistor. The cell structure is formed in defect-free layer 16 of P type substrate 11 and over that substrate. That is, the cell structure comprises first poly-Si layer (capacitor electrode) 20, MOS capacitor made up of 21a and N$^-$ layer 22, and NMOS FET formed of N$^+$ layer 23 constituting a drain and source, second poly-Si layer (gate electrode) 24 and gate oxide film 21b in which case a great number of cells are connected together by aluminum wiring 25 and so on. FIG. 7 shows an electric equivalent circuit. When data "1" is written into the cell, a corresponding charge is formed in the MOS capacitor and, after the completion of a write-in operation, the MOS FET is brought back to an "OFF" state and separated from the MOS capacitor to retain induced charge. The charge is released upon the lapse of time and vanishes. It is, therefore, necessary to perform a data read/write (refresh) operation at each predetermined time. The BMD, if left in defect-free layer 16, hastens the release of the induced charge and shortens what is called a charge retaining time (pause time). FIG. 8 is a graph showing a variation in the pause time of the respective bits within one chip. In the graph shown, the left side portion shows the result of the conventional method and that of the present method where the ordinate denotes the pause time in an arbitrary measurements unit and the abscissa the number of bits in units of 100 Kbits. As seen from the graph, the product manufactured in accordance with the conventional method includes those cells of a short pause time, meaning that BMDs are still left in defect-free layer 16 and function as the generation center or recombination center of carriers. On the other hand, the pause time of the product of the present invention is longer and narrower in its distribution and less in its variation and hence the product is stable in quality.

In the aforementioned embodiment, the concentration of H$_2$ in a gaseous atmosphere at the step of forming a well region is about 10% in terms of a volume ratio. From the results of tests made at a varying H$_2$ concentration it is seen that the H$_2$ concentration needs to be at least 1% in terms of the volume ratio. At the concentration of less than 1%, it is often impossible to obtain an adequate DZ width. A desired effect can be obtained even at a higher concentration of the H$_2$ gas, provided that an extra operation is required, for example, in the handling of the H$_2$ gas.

Although, in place of an N$_2$ gas, an inert gas, such as Ar, Ne and He, or a combination thereof, may be employed, it is desirable to use N$_2$ or Ar in terms of their cost involved.

Figure 9:
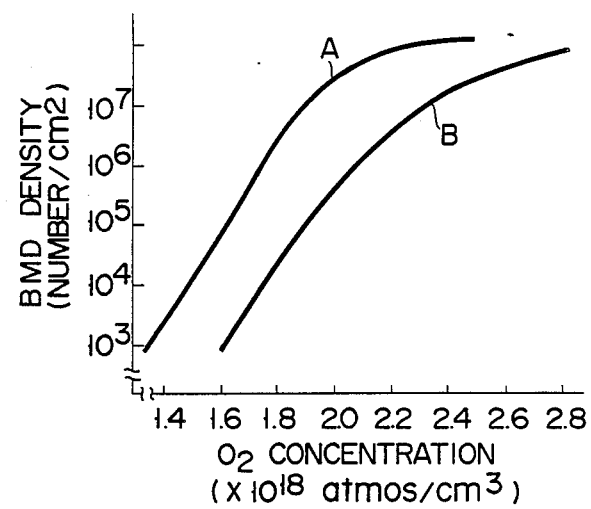
FIG. 9 is a graph showing a relation of an average BMD density at a middle of a gettering portion to the concentration of $O_2$ which is contained in a wafer as manufactured in accordance with a CZ method and MCZ method.

The DZ width and gettering portion as formed in the substrate in accordance with the present invention is largely affected by the concentration of oxygen in the wafer used. FIG. 9 shows curves representing a relation of the oxygen concentration (atoms/cm$^3$) to an average BMD density (number/cm$^2$) at the middle of the gettering portion, noting that the data was measured after the process of the aforementioned 1M DRAM using a wafer formed in the CZ method (the curve A) and that in the MCZ method. For a lower oxygen concentration, the generation density of BMDs is decreased, failing to obtain an adequate gettering effect. For a higher oxygen concentration, on the other hand, it is sometimes impossible to obtain a desired DZ width. It is desirable that the oxygen concentration of the wafer be $1.4 \times 10^{18}$ to $3 \times 10^{18}$ atoms/cm$^3$.

Although, in the aforementioned embodiment, the semiconductor device, such as a DRAM, has been explained in connection with, for example, an N well area in a deep impurity diffusion area of the DRAM, the present invention is not restricted to the aforementioned embodiment. The present invention can equally be applied to the manufacture of a semiconductor device, including a step of performing a heat treatment at over 1100° C. as in the initial phase of the manufacturing process.

According to the manufacturing method of the present invention, as set out in connection with the aforementioned embodiment, the generation of BMDs still present near the surface of the substrate when the conventional IG method is employed is largely suppressed to obtain a defect-free layer of an adequate DZ width. It is thus possible to form a gettering portion with a high-density BMD distribution and hence to improve the characteristics and yield of the present invention. Furthermore, it is also possible to obtain a highly reliable semiconductor device because the generation of the BMDs present near the surface layer of the substrate is largely suppressed and hence because nuclei are formed due to oxygen penetrating the oxide film on the substrate.

What is claimed is:

1. A method for manufacturing a semiconductor device having in a semiconductor substrate of one conductivity type a deep island-like diffusion layer of the opposite conductivity type, said method suppressing the generation of bulk microdefects near the substrate surface layer and comprising the steps of:

selectively forming in the semiconductor substrate of one conductivity type a deep island-like impurity diffusion layer of the opposite conductivity type, including the substeps of,
  forming an oxide film on the semiconductor substrate;
  forming a resist pattern on the oxide film;
  implanting an impurity ion into the substrate at a predetermined location;
  forming a well by heating the substrate at a temperature greater than 1100° C. in a gas comprising H$_2$ and one of N$_2$, Ar, Ne, He or a mixture thereof; and
  removing the oxide film;
forming a field oxide film, serving as an element isolation layer, next to the impurity diffusion layer;
forming a first gate, serving as a capacitor, on the semiconductor substrate;
forming a second gate, serving as a switching transistor, on the semiconductor substrate and connected in parallel with the first gate;
forming an insulation layer for insulating the first gate from the second gate; and
forming a passivation film for protecting an element uppermost on the insulation layer.

2. The method according to claim 1, wherein a volume ratio of said $H_2$ gas to said one of $N_2$, Ar, Ne, He and a mixture thereof is greater than approximately 1%.

3. The method according to claim 1, in which said semiconductor substrate is placed in an $H_2$ concentration atmosphere of $1.4 \times 10^{12}$ to $3.0 \times 10^{18}$ atoms/cm$^3$ to form said well, said $H_2$ concentration being found from an equation $$(\alpha \times 4.81 \times 10^{17}) \text{ atoms/cm}^3$$

where
  $\alpha$: an absorption coefficient (cm$^{-1}$) of an infrared radiation whose wave number is 1106 cm$^{-1}$.

4. The method according to claim 2, in which said semiconductor substrate is placed in an oxygen concentration atmosphere of $1.44 \times 10^{18}$ to $3.0 \times 10^{18}$ atoms/cm$^3$ to form said oxide film, the oxygen concentration being found from an equation $$(\alpha \times 4.81 \times 10^{17}) \text{ atoms/cm}^3$$

where
  $\alpha$: an absorption coefficient (cm$^{-1}$) of an infrared radiation whose wave number is 1106 cm$^{-1}$.

* * * * *